United States Patent [19]
Ito et al.

[11] Patent Number: 5,176,854
[45] Date of Patent: Jan. 5, 1993

[54] NON-LINEAR OPTICAL DEVICE

[75] Inventors: Yuzo Ito, Hitachi; Hiromu Terao, Katsuta; Kayo Ono, Hitachi; Sukekazu Aratani, Hitachi; Masato Isogai, Mito; Atsushi Kakuta, Hitachiota, all of Japan

[73] Assignee: Hitachi, Ltd., Tokyo, Japan

[21] Appl. No.: 711,414

[22] Filed: Jun. 5, 1991

Related U.S. Application Data

[63] Continuation of Ser. No. 265,992, Nov. 2, 1988, abandoned.

[30] Foreign Application Priority Data

| Nov. 2, 1987 | [JP] | Japan | 62-275768 |
| Nov. 20, 1987 | [JP] | Japan | 62-293398 |
| Feb. 5, 1988 | [JP] | Japan | 63-23821 |
| Mar. 4, 1988 | [JP] | Japan | 63-49558 |

[51] Int. Cl.$^5$ ............ F21V 9/04; G02B 6/00; C07D 311/82; C07D 311/80
[52] U.S. Cl. .................... 252/582; 252/587; 252/589; 359/328; 359/350; 359/361; 359/329; 549/392; 549/394; 549/391
[58] Field of Search ............ 252/582, 587, 589, 600; 549/388, 391, 394, 392; 568/308, 332, 326, 924; 359/350, 351, 352, 353, 354, 355, 356, 357, 358, 359, 360, 361, 328, 329

[56] References Cited

U.S. PATENT DOCUMENTS

| 4,759,820 | 7/1988 | Calvert et al. | 252/582 |
| 4,774,025 | 9/1988 | Choe et al. | 252/582 |
| 4,909,608 | 3/1990 | Frazier, III | 350/354 |
| 4,946,261 | 8/1990 | Yaegashi et al. | 350/353 |

OTHER PUBLICATIONS

Frazier, C. et al., J. Opt. Soc. Amer. B. 4(11), 1899–1902, (1987).
Williams, D. J. Angew. Chem. Int. Ed. vol. 23, pp. 690–703, (1984).
Okogun, J. et al., J.C.S. Chem. Comm. p. 8, 1975.
Coda, A. et al., J. Appl. Cryst. 9, 193, 1976.
Tweig, R. J. Organic Materials for second harmonic generation: Report UCRL-15706 1985: CA106:57923q.

Primary Examiner—Robert L. Stoll
Assistant Examiner—Philip Tucker
Attorney, Agent, or Firm—Antonelli, Terry, Stout & Kraus

[57] ABSTRACT

According to the present invention, there is provided a non-linear optical device comprising a non-linear optical medium comprising an organic compound, which remarkably improves the non-linear optical properties. The non-linear optical device according to the present invention is suited for the second and third harmonic generations, photomixing optical parametric oscillations, optical switches and optical bistable devices.

7 Claims, 6 Drawing Sheets

NON-LINEAR OPTICAL DEVICE

This application is a continuation of application Ser. No. 07/265,992, filed on Nov. 2, 1988 now abandoned.

BACKGROUND OF THE INVENTION

This invention relates to non-linear optical devices, and more particularly to a non-linear optical device provided with organic materials which show a splendid non-linear optical effect.

An optical device according to this invention may be utilized for generating second and third harmonic waves, optically mixing parametric oscillations, optical switches, optical bistable devices, and the like.

A non-linear optical device according to the invention refers to an optical device which makes optical modulations based on the principle of operation of the non-linear optical effect, see Max Schubert and Bernd Wilhelmi: "Nonlinear Optics and Quantum Electronics", John Wiley & Sons (1986).

The non-linear optical effect has been utilized as the basic principle of various optical modulation elements. For example, the second harmonic generation (SHG) as a secondary non-linear optical effect has been widely used to generate a double wave (wavelength: 532 nm) of which wavelength is half short that of the Nd-YAG laser basic wave (wavelength: 1064 nm), for exciting a dye laser, and parametric oscillations are also used to generate near infra-red pulse beams.

Both Pockels effect and Kerr effect known as the electro-optical effect are kinds of non-linear optical effects and they both have the principle of operation of the optical switch as the object.

The non-linear optical device can be used as the elements of the harmonic generation, optical mixing, optical parametric oscillations, optical switches by utilizing secondary and tertiary non-linear polarizations of the electromagnetic fields. Also it has been attracting attention as an optical bistable device which can serve as basic elements of optical computers of which the realization is anticipated in the future.

Conventionally, inorganic materials and semiconductor materials such as lithium niobate ($LiNbO_3$), potassium dihydrogenphosphate ($KH_2PO_4$, generally called as KDP), gallium arsenide have been considered as materials for attaining the non-linear optical device effect. But, in recent years, organic non-linear optical materials having an extremely high optical reaction rate which are excellent in non-linear optical performance (10–1000 times) compared with those of the above-mentioned and are important for optical bistable devices, etc. have been discovered successively, and the non-linear optical devices utilizing the above mentioned optical bistable devices have been actively developed.

Specific examples of the organic non-linear optical materials are urea, 2-methyl-4-nitroaniline (hereafter referred to as MNA) (JP-A-55-50096), N-(4-nitrophenol)-L-prolinol (hereafter referred to as NPP) (JP-A-59-21665) and the like. In particular, MNA or NPP is known to have a non-linear optical constant more than 100 times that of inorganic materials.

However, the above mentioned organic non-linear optical devices have the following problems and are difficult to be put into practical use.

Firstly, although urea is a material having an absorption in the visible region and has phase matching conditions, its non-linear constant is nearly the same as that of the inorganic materials. Therefore, it has little advantages and it is difficult to treat urea due to its water solubility.

On the other hand, each of MNA and NPP has a large non-linear optical constant and an excellent fundamental properties. On the contrary, these materials have some problems in that a large single crystal which is excellent in quality is difficult to be made, they are inferior in stability, resistance, etc., and the cutoff wavelength is longer, that is, the optical absorption takes place within the visible range.

Especially, the problem of length of the cutoff wavelength needs to be improved from the viewpoint of the practical use such as, for example, application to frequency conversion elements of the second harmonic generation (SHG) and the like. This is also the same when optical processing in the visible range as well as the frequency conversion element of the second harmonic generation (SHG) are taken into consideration.

In MNA, the cutoff wavelength is 480 nm and in NPP it is approximately 490 nm. Accordingly, they may be considered to be unstable as the materials for frequency conversion elements of SHG of the currently-used semiconductor laser wavelength: approximately 800 nm).

Especially, heat stability should be improved from the viewpoint of the practical use. Generally, the optical damage threshold value (momentary optical resistance) of the excellent organic non-linear optical materials is much larger than that of the inorganic materials.

However, the resistance of the organic materials when exposed to light for a long time is not so large, because the light energy is converted into heat and the organic materials usually have a poor heat resistance.

Therefore, heat stability becomes a very important feature in considering practical stability and resistance of organic non-linear optical materials. From this point of view, it is desired that organic non-linear optical materials should have a high melting points (more than 200° C.). Prior to the present invention, organic materials having a great non-linear capability and being in conformity with the above mentioned condition have not yet been found. Especially, the heat resistance of the material should be greatly improved when consideration is given to light treatment with high output. The present inventors are the first to find the materials which satisfy all the requirements as an excellent non-linear optical material which have been left to be found in organic non-linear optical materials.

SUMMARY OF THE INVENTION

An object of this invention is to provide a non-linear optical device using stable organic non-linear optical materials with a large non-linear optical constant and a short cutoff wavelength.

In order to attain the above mentioned object, designing is required at the level of the molecular structure. Generally, organic materials having a large non-linear optical constant have the following characteristics in their molecular structures.

The molecule contains a $\pi$-electron conjugated system where electrons are localized by the substituents or atoms in the molecule. Also, the symmetry of molecule is deformed by the carbon skeleton or the substituents.

When such characteristics are prominent, non-linear optical properties improve, but the cutoff wavelength becomes longer accordingly (see FIG. 10). This is a dilemma in attaining the above mentioned objects.

Therefore, detailed designing of the molecule is required for attaining the object of shortening the cutoff wavelength.

In the first place, in order to show a large non-linear optical constant as a molecule, it is desirable that there should be a $\pi$-electron conjugated system in the molecule, which further contains at least one electron donating group and/or at least one electron withdrawing group as a substituent. But this is only a general view and it is quite difficult to determine the suitable carbon skelton containing a $\pi$-conjugated system or the suitable substituents.

Moreover, molecules exist cohered and the non-linear optical properties are greatly influenced by the way molecules gather when they are crystallized or thin filmed. In order to draw out the non-linear optical effect efficiently, attention should be paid to the rowing of each molecule in the material.

Detailed molecule design is also required for this purpose.

Moreover, when the organic non-linear optical material is required to have heat resistant stability, that is, an elevated melting point, besides the above mentioned features, considerations should be paid to the increase in aggregation energy at the crystal formation and in entropy at melting.

Prior to the present invention, it was impossible to obtain a material for non-linear devices having a short cutoff wavelength and a large $\beta$ value. The present inventors are the first to find such a compound not having a crystalline structure having an inversion center, it is now possible to obtain a non-linear optical device exhibiting excellent properties (see FIG. 11).

Exemplary to the present invention, but not limiting thereto, there are provided (a) a compound having the formula:

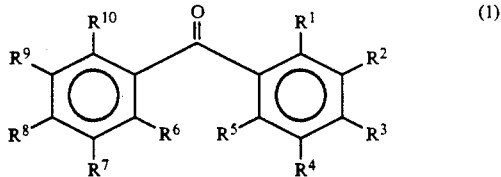

(1)

wherein $R^5$ and $R^6$ are both hydrogen, or $R^5$ and $R^6$, when taken together, form a single bond or a —X— bond (X is O, S or NH), and, all of $R^1$ to $R^4$ and $R^7$ to $R^{10}$ are hydrogen, or at least one of them is at least one member selected from the group consisting of —NH$_2$, —NHCH$_3$, —N(CH$_3$)$_2$,

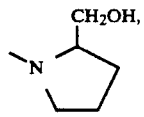

—OC$_n$H$_{2n+1}$ (n is an integer of 1-5), —SC$_n$H$_{2n+1}$ (n is an integer of 1-5), —NO$_2$, —CN, —CY$_3$ (Y is a halogen), —COC$_n$H$_{2n+1}$ (n is an integer of 1-5), —OH, —Cl, —Br, —F, —C$_n$H$_{2n+1}$ (n is an integer of 1-5),

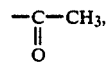

and the rest are hydrogen; (b) a non-linear optical device comprising a non-linear optical medium comprising said compound; (c) a non-linear optical device comprising a non-linear optical medium comprising said compound in a transparent polymer; and (d) a non-linear optical device comprising a non-linear optical medium comprising a transparent polymer containing said compound in the side chain of a transparent polymer.

Three types of the compounds which are included in the non-linear optical medium of non-linear optical devices according to this invention are shown as follows:

(A) A compound, according to the above formula (1), wherein both $R^5$ and $R^6$ are hydrogen, that is, benzophenone and benzophenone derivatives.

(B) A compound, according to the above formula (1), wherein both $R^5$ and $R^6$ are taken together and form a single bond, that is, fluorenone and fluorenone derivatives.

(C) A compound, according to the above formula (1), wherein $R^5$ and $R^6$ are taken together and form a —X— bond through X (X is O, S or NH).

The non-linear optical medium, included as part of the non-linear optical device, can include an agglomerate of the compound having the above formula (1). Alternatively, segments of the compound of the above formula (1) can be included as part of an organic polymer, e.g., a transparent organic polymer. For example, compounds of the above formula (1) can be bound to a side chain of a transparent organic polymer. The presently set forth techniques for including the compound of the present invention in the non-linear optical medium of the non-linear optical device of the present invention is merely illustrative, and not limiting for the present invention.

DETAILED DESCRIPTION OF THE INVENTION

Figure 1:
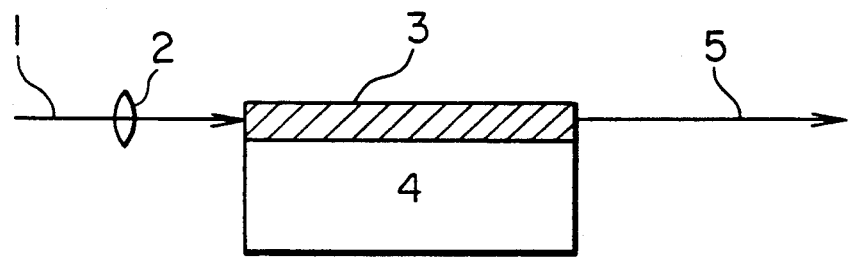
FIG. 1 is an explanatory drawing of an embodiment of the organic non-linear optical device according to this invention.

In FIG. 1, 1 shows a laser beam, 2 lens, 3 an organic non-linear optical medium of a thin film, 4 a base, 5 a second harmonic wave.

Figure 5:
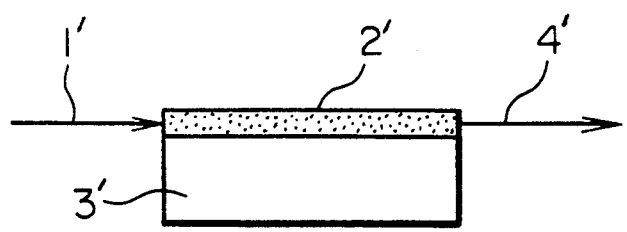
FIG. 5 is a cross-sectional view of a frequency conversion element as an embodiment of the invention.
Figure 6:
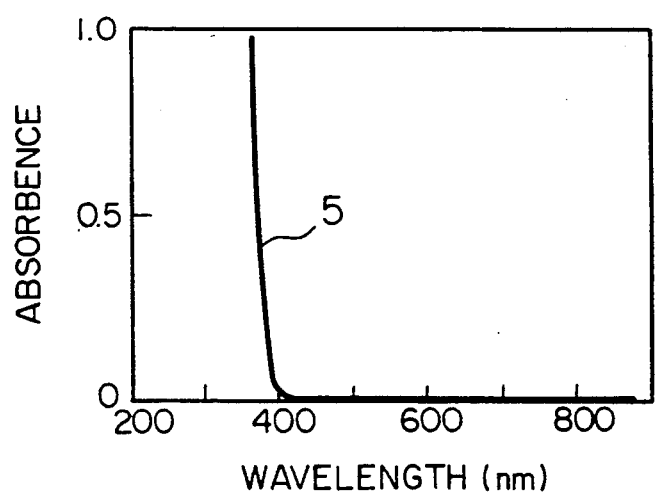
FIG. 6 shows an absorption spectrum of 4-methoxyl-4-nitrobenzophenone as an example of the non-linear medium according to the invention.

In FIGS. 5 and 6, 1' shows an incident laser beam, 2' a non-linear optical medium, 3' a base, 4' an outgoing second harmonic, 71, 72 incident laser beams, 8 a non-linear optical medium, 9 an outgoing second harmonic wave.

In a compound of Type (A) discussed above, wherein both $R^5$ and $R^6$ are hydrogen, the presence of the substituent is not critical. Preferably, 1–3 of $R^1$ to $R^4$, $R^7$ to $R^{10}$ are the substituents mentioned above.

"n" in $-OC_nH_{2n+1}$, $-SC_nH_{2n+1}$, $-COC_nH_{2n+1}$, $-C_nH_{2n+1}$ is preferably an integer of 1 to 3, and m preferably 1.

And more preferably, one or two electron donating groups or one or two electron withdrawing groups are attached to the phenyl, which groups are selected from the substituents shown above. Furthermore, preferable are bisubstituted compounds which contain a set of an electron donating group and a non-electron donating group, or a set of an electron withdrawing group and a non-electron withdrawing group, whereby non-linearity of the non-linear optical devices according to the invention can be strengthened.

In this invention, the electron donating group refers to an atom or a group having the properties of offering electrons to the $\pi$-electron system in the electronic theory in organic chemistry.

For example, the following can be listed: $-NH_2$, $-NHCH_3$, $-N(CH_3)_2$,

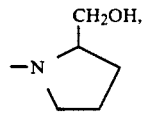

$-OH$, halogens, etc.

In this invention, electron withdrawing group refers to an atom or a group having the properties of withdrawing electrons from the $\pi$-electron system in the electronic theory in organic chemistry.

For example, the following can be listed: $-NO_2$, $-CN$, $-CY_3$ (Y is a halogen), $-COCH_3$, $-COOCH_3$, etc.

In this invention, the neutral group refers to an atom or a group having weak properties to donate electrons to the $\pi$-electron system or to withdraw electrons from the $\pi$-electron system in the electronic theory in organic chemistry.

The expression "non-electron donating group" means a group including the electron withdrawing group and the neutral group. The expression "non-electron withdrawing group" is defined as a group including the electron donating group and the neutral group.

Specific examples thereof are alkyloxy groups ($-OC_nH_{2n+1}$) and alkylthio groups ($-SC_nH_{2n+1}$) Naturally, hydrogen is neutral but it is not deemed as a substituent. The position of the substituent is not critical. Preferable are the position of $R^2$ and $R^8$, $R^3$ and $R^8$ or $R^2$ and $R^7$.

Typical examples are as follows: 4-methoxy-4'-nitrobenzophenone, 4-amino-4'-nitrobenzophenone, 4-methylamino-4'-nitrobenzophenone, 4-prolinoyl-4'-nitrobenzophenone, 4-methoxy-4'-aminobenzophenone, 4-methoxy-4'-dimethylaminobenzophenone, 4-thiomethyl-4'-dimethylaminobenzophenone, as well as compounds containing cyano, trifluoromethyl, acetyl (for example, 4-amino-4'-cyanobenzophenone, 3-amino-4'-methoxybenzophenone, 3-nitro-3'-methoxybenzophenone, 3-nitro-4'-methoxybenzophenone, 4-methoxy-4'-methylaminobenzophenone, 4-methylamino-4'-thiomethylbenzophenone, 4-dimethylamino-4'-thiomethylbenzophenone, 4-ethylamino-4'-thiomethylbenzophenone, etc.) at $R^3$ position instead of nitro group.

Compounds of Type (A) can be prepared by a known process, see Beilstein, E III 8, 1247-9. Generally, these compounds can be prepared in accordance with the following process:

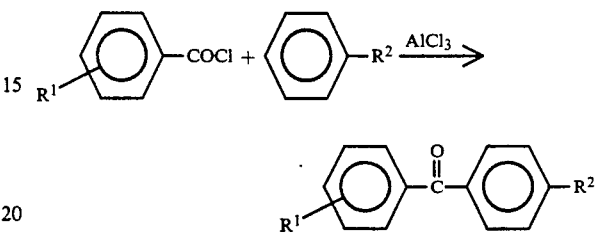

For example, 4-methoxy-4'-nitrobenzophenone can be prepared as follows:

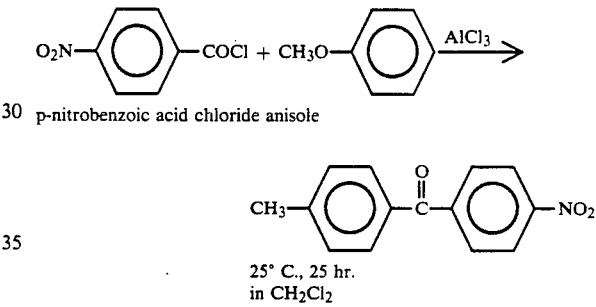

p-nitrobenzoic acid chloride anisole

25° C., 25 hr.
in $CH_2Cl_2$

NMR $\delta=3.87$ (s), 6.95 (d), 7.77 (d), 7,80 (d), 8.27 (d)

In the compounds of Type (B), wherein both $R^5$ and $R^6$ are taken together and form a single bond, the presence of the substituents is not critical. Preferably, 1 to 3 positions in $R^1$ to $R^4$ and $R^7$ to $R^{10}$ are substituted by the substituents selected from the above example. "n" in $-OC_nH_{2n+1}$, $-SC_nH_{2n+1}$, $-COC_nH_{2n+1}$, $-C_2H_{2n+1}$ should preferably be an integer of 1 to 3 and more preferably 1.

And more preferably, one or two positions are substituted by one or two of the electron donating groups or electron withdrawing groups. Furthermore, preferable are bisubstituted compounds which contain a set of an electron donating group and a non-electron donating group, or a set of an electron withdrawing group and a non-electron withdrawing group, whereby non-linearity of the non-linear optical devices according to the invention can be strengthened.

As examples thereof, the following fluorenone derivatives can be listed: 2-fluoro-9-fluorenone, methyl 7-nitro-9-oxo-4-fluorenecarboxylate, 2,7-dinitro-9-fluorenone, 2-nitro-6-amino-9-fluorenone, 2-nitro-6-dimethylamino-9-fluorenone.

The type (B) compounds can be prepared or can be available as follows: 2-nitro-9-fluorenone (Aldrich 29975-8), 2-fluoro-9-fluorenone (Aldrich F900-0), Methyl 7-nitro-9-oxo-4-fluorenecarboxylate (Aldrich 30017-9) etc. are commercially available.

Generally, fluorenone derivatives can be prepared by the oxidation thereof, see Reagents for Org. Synthe. 3, 150,

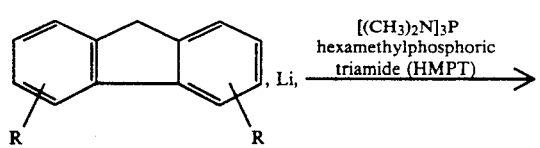

fluorene and also, 2,7-dinitro-9-fluorenone can be available through a known method, see Beilstein, E III 7, 2347.

As for the type (C) compounds, wherein $R^5$ and $R^6$ are taken together and form an -X- bond through X (X is O, S or NH), the presence of substituents is not critical. Preferably, 1 to 3 positions among $R^1$ to $R^4$, and $R^7$ to $R^{10}$ are substituted. "n" in $-OC_nH_{2n+1}$, $-SC_nH_{2n+1}$, $-COC_nH_{2n+1}$, and $-C_nH_{2n+1}$ is preferably an integer of 1 to 3 and more preferably 1.

And more preferably, 1 or 2 positions are substituted by 1 or 2 electron donating groups or 1 or 2 electron withdrawing groups. Furthermore, bisubstituted compounds are preferable, which contain a set of an electron donating groups and a non-electron donating groups, or a set of an electron withdrawing group and a non-electron withdrawing group, whereby the non-linearity of the non-linear optical devices according to this invention can be strengthened.

When X is O (oxygen) in the type (C) compounds, they are xanthone or xanthone derivatives. It is preferable that, in this invention, xanthone is substituted with at least one electron withdrawing group or electron donating group. Furthermore, it is preferable that xanthone contains such substituents (bulky groups such as an alkyl group such as methyl) that prevent the molecule having a center of symmetry when it is crystallized.

Specific examples of the xanthone derivatives which can be used in this invention are as follows. 1-nitroxanthone, 2-nitroxanthone, 3-nitroxanthone, 4-nitroxanthone, 6-amino-1-nitroxanthone, 6-amino-2-nitroxanthone, 5-methyl-2-nitroxanthone, 5-chloro-2-nitroxanthone, 2-Bromo-1-nitroxanthone, 2-bromo-3-nitroxanthone, 1,7-dinitroxanthone, 2,7-dinitroxanthone, 2,4-dinitroxanthone, 2,7-diaminoxanthone, 1,3-dihydroxy-7-methoxyxanthone, 1-chloro-7-hydroxy-4-nitroxanthone, 1-chloro-7-methoxyxanthone, 4-methyl-7-nitroxanthone, 3-aminoxanthone, 1-amino-6-nitroxanthone, 2-methyl-7-nitroxanthone.

Generally, the type (C) compounds can be prepared through the following reaction scheme.

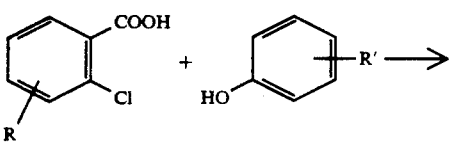

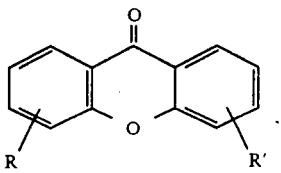

For example, 2,7-dinitroxanthone can be prepared through the following known process.

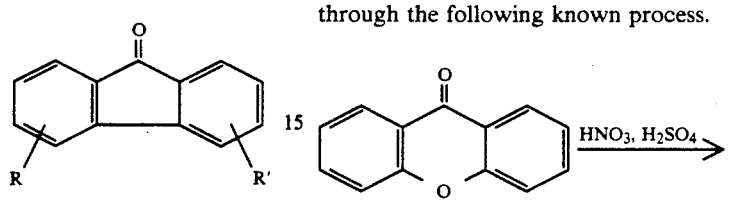

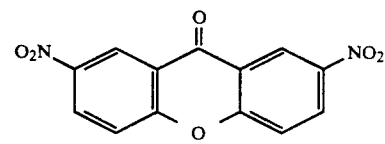

And 2,7-diaminoxanthone can be prepared as follows, see M. Julia, Mémoires présentés à la société chimique, 1952, 546.

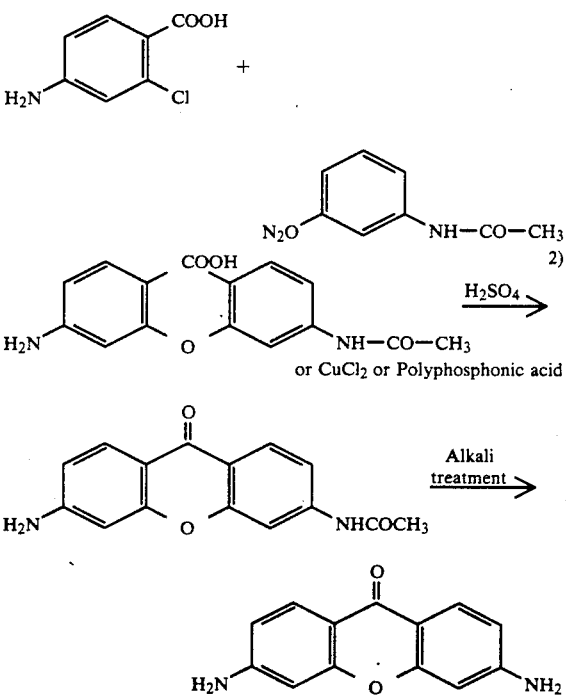

1) Reagents for Org. Synthe. 6, 138
2) Reagents for Org. Synthe. 4, 395

The compounds according to this invention may be used alone as non-linear optical materials but they can also be used as a combination with transparent polymers.

The transparent polymer refers to a polymer or a copolymer having a visible light transmittance through a 10 mm thick sample of more than 90%.

Specific examples thereof are acrylic acid, methylacrylate, ethylacrylate, butylacrylate, isobutylacrylate, n-butyl methacrylate, isobutyl methacrylate, triethyl propanemethacrylate, n-hexyl methacrylate, cyclohexyl methacrylate, phenyl methacrylate, benzyl methacrylate, ethylene glycol dimethacrylate, glycydyl methacrylate, pentafluorobutyl methacrylate, styrene, chlorostyrene, 2,5-dichlorostyrene, bromostyrene, methylstyrene, methoxystyrene, polysiloxane and the fluoro-substituted derivatives thereof.

The method for mixing is not critical and a known method may be applied. The mixing ratio is not critical so far as the compound according to this invention is not microcrystallized in the transparent polymer. Preferably, it is less than 20% by weight, more preferably less than 15% by weight.

The compound according to this invention can be used by introducing it into the side chains of the transparent polymer.

Such polymer can be obtained by mixing and copolymerizing the compounds according to this invention and the monomer of the transparent polymer. Their bonds are ether linkage, ester linkage or carbon-carbon bond, which may have spacers comprising a carbon chain.

Specific examples of the transparent polymers containing the compounds according to the invention at the side chain are acrylic acid, methacrylic acid, styrene, ethylene, polysiloxane and the copolymers thereof and the fluoro polymers or copolymers of the above-mentioned ones.

The content of the compounds according to the invention bound to the polymer is not critical. Usually, the number of moles of the compound is the same as or less than that of the monomer.

The compounds according to the present invention have no symmetry of inversion even when they gather. The non-linear polarization vectors are preferably aligned in the same direction and almost in parallel in order to gain a larger $\chi^{(2)}$.

The orientation of the molecules by poling at the time of or after the polymerization improves the non-linear optical properties of the product.

The poling is preferably carried out by applying high electric fields of approximately $10^6$ V/cm at a temperature of more than the glass transition temperature Tg of the transparent polymer.

The materials of the base of the optical devices are not critical and commercially available ones may be used. And the shape thereof is not critical either.

The following examples serve to give specific illustrations of the practice of the present invention but they are not intended in any way to limit the scope of the present invention.

EXAMPLE 1

Molecular structures of fluorenone and its derivatives were studied by the molecular orbital method to determine the values of maximum excited wavelength $\lambda$ of the molecule with the aid of the complete neglect of differential overlap, configuration interaction, method, CNDO/S3-Cl.

In the next stage, the value $\beta$ of each sample was measured by the dc-SHG method. More concretely, the sample was dissolved in ethanol and then the pulse voltage of 5 kV, 2 $\mu$s was applied thereto. In synchronizing with it, pulse YAG laser beam (wavelength: 1.06 $\mu$m) of 10 ms with the peak power 100 MW was irradiated to the sample and the frequency-converted light having a wavelength of 530 nm was measured by the photomultiplier tube. The value $\beta$ was estimated based on the output from the pure liquid of nitrobenzene, which was measured in the same manner as described above. Table 1 shows the calculated values of $\beta$ and $\lambda$max and the measured values of $\beta$. Table 1 also shows the value of MNA concurrently for comparison.

TABLE 1

| Name & Molecular structure | Calculated Value $\beta(10^{-30}\text{esu})$ | $\lambda_{MAX}(\text{nm})$ | Observed Value $\beta(10^{-30}\text{esu})$ |
|---|---|---|---|
| 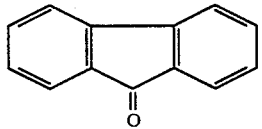 9-fluorenone | −5.7 | 354 | 2.5 |
| 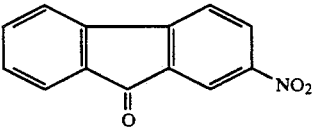 2-nitro-9-fluorenone | 13.7 | 358 | 7.2 |
| 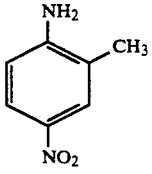 MNA | 9.0 | 288 | 7.0 |

Next, the non-linear optical constant of the crystal was measured by the Powder Method. For the first time, after the grains of the sample were leveled to approximately 100 $\mu$m in diameter by grinding the sample in a mortar, the SHG strength was measured by irradiating Q-switch YAG laser beams, by converging the frequency-converted light of 530 nm in wavelength with a condenser lens, and cutting the lights other than 530 nm with various kinds of filters. Table 2 shows the measured results represented by the relative ratio of the same to urea.

Figure 2:
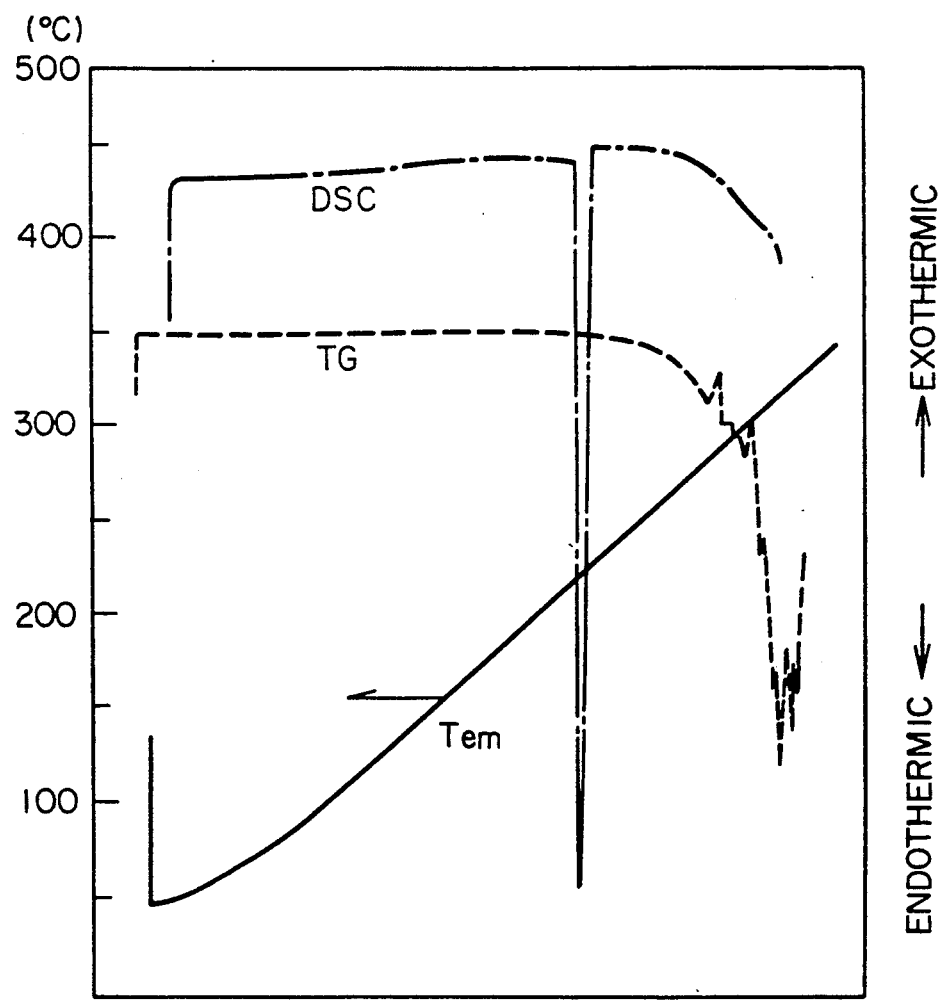
FIG. 2 is TG-DSC curve of 2-nitro-9-fluorenone, an example of a non-linear optical medium according to the invention.

In the next stage, TG (Thermogravimetry) DSC measurement was made in order to examine the heat stability. As for the melting point, the results are shown in Table 2. Concerning TG-DSC measurement, the result on 2-nitro-9-fluorenone is shown in FIG. 2 as a typical example. On reviewing this, it is clear that 2-nitro-9-fluorenone is very stable in heat up to the melting point of 223° C. and not causing thermal decomposition.

TABLE 2

| Chemical compound | Powder SHG efficiency (× urea) | Melting point (°C.) |
| --- | --- | --- |
| 2-Nitro-9-fluorenone | 25 | 235 |
| Methyl-7-nitro-9-oxo-4-fluorene carboxylate | 1.5 | 203 |
| MNA | 22 | 153 |

EXAMPLE 2

FIG. 1 shows a schematical drawing of a frequency conversion element which utilizes the second harmonic generation. Fluorenone and its derivatives were used for the non-linear optical device. The element can be made by growing a thin film monocrystal on the base by the epitaxial growth method. When the phase matching condition is applicable to the materials, the bulk single crystal of the material itself can be made into elements. In this case, the single crystal can be obtained by slowly cooling the saturated ethanol solution thereof starting from 60° C. in a constant temperature bath at the rate of 0.03° C. per hour. The second harmonic wave of 530 nm in wavelength was measured with the photomultiplier tube by passing YAG laser beams (wavelength: 1.06 μm) having the peak power of 100 kW, 100 ps through the elements. Conversion efficiency of 2-nitro-9-fluorenone was twenty times that of urea.

EXAMPLE 3

The following is a preparation example of polymers containing fluorenone and its derivatives as a composition. 10 Grams of 2-nitro-9-fluorenone were dissolved in 50 g of methyl methacrylate and 0.02% by weight of lauroyl peroxide was added thereto as a polymerization initiator. Then, they were polymerized for 48 hours at 60° C. To the polymerized composition thus obtained was applied poling treatment so that the molecules were oriented. The composition was made into the element. Conversion efficiency of YAG laser beams to the second harmonic wave was determined by the same operation as in Example 2. The result was 15 times that of urea.

EXAMPLE 4

The structure of frequency conversion elements utilizing the second harmonic generation is shown in FIG. 1. As a non-linear optical medium, a xanthone derivative containing at least either one of the electron donating group or the electron withdrawing group was used. A thin film single crystal was grown on the base 4 by the epitaxial growth method to make the element. When the phase matching condition is applicable to molecules, the bulky single crystal thereof can be made into the element. The sample of single crystal in this case can be obtained by slowly cooling the saturated ethanol solution starting from 60° C. to 20° C. in a constant temperature both at the rate of 0.02° C. per minute.

The second harmonic of 532 nm (frequency-converted light) 5 was measured with a photomultiplier tube by passing YAG laser beams (wavelength: 1064 nm) having a peak power of 100 kW, 100 ps through the element. Conversion efficiency of 2-nitroxanthone was approximately 2.3 times that of urea.

EXAMPLE 5

The structure of xanthone derivatives containing at least either one of the electron donating group or the electron withdrawing group was studied by the molecular dynamic method and the molecular orbital was calculated by the CNDO S3-CI. The hyperpolarizability $\beta$ and the maximum excitation wavelength $\lambda_{max}$ were estimated on the basis of the result of the calculation.

The examples of the results are shown in Table 3. The results of the calculation of xanthone itself is shown as a reference.

TABLE 3

| | $\beta_{YYY}(\times 10^{-30}\text{esu})$ | $\lambda_{max}$(nm) |
| --- | --- | --- |
| xanthone 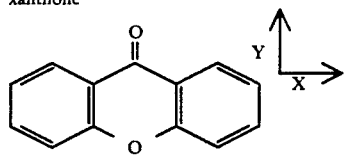 | −3.11 ($\beta_{XXY}$, −4.70) | 302 |
| 2-nitroxanthone 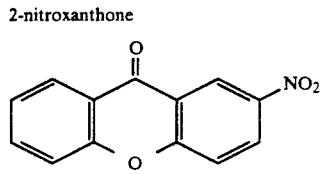 | −2.78 ($\beta_{XXY}$, −7.64) | 297 |

TABLE 3-continued

| | $\beta_{YYY}(\times 10^{-30} \text{esu})$ | $\lambda_{max}(\text{nm})$ |
|---|---|---|
| 3-nitroxanthone | −3.26 ($\beta_{XXY}$, −2.49) | 315 |
| 2,7-dinitroxanthone | −2.5 ($\beta_{XXY}$, −10.5) | 297 |
| 6-amino-1-nitroxanthone | −4.5 ($\beta_{XXX}$, −10.4) | 368 |

The following each sample was measured for dc-SHG. The sample was dissolved in ethanol and pulse voltage of 5 kV, 2 μs was applied thereto. In synchronizing with that, a frequency-converted light of 532 nm in wavelength was measured with a photomultiplier tube by irradiating YAG laser beams (wavelength: 1,064 nm) having a peak power of 100 MW, 10 ns. The value $\beta$ was estimated by using an output light of the pure liquid of nitrobenzene, which was measured in the same manner as the reference.

Figure 3:
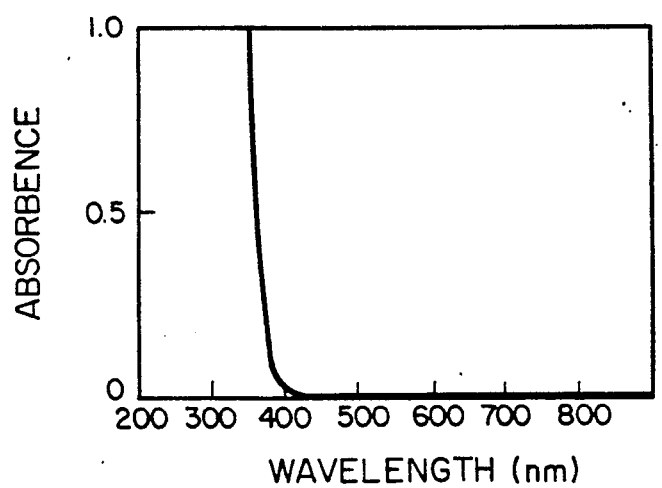
FIG. 3 shows an absorption spectrum of 2-nitroxanthone as an example of the non-linear optical medium.
Figure 4:
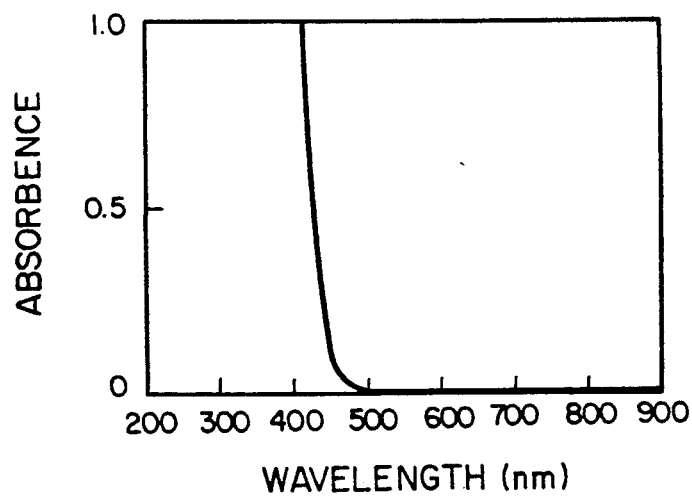
FIG. 4 shows an absorption spectrum of 2-nitro-4-nitroaniline as an example for comparison.

Furthermore, 0.001 mol/l of the ethanol solution of the sample was prepared, and the absorption spectrum thereof was measured with a spectro-photometer. The absorption spectrum of 2-nitro-xanthone is shown in FIG. 3 as an example, The absorption spectrum of MNA in the same solvent having the same density is shown in FIG. 4 as a comparative example. It is clear that in the case of MNA, the absorption spectrum starts rising at about 480 nm but in the case of 2-nitroxanthone, the spectrum starts rising at about 380 nm and the cutoff wavelength ($\lambda c$) is on the shorter wavelength side. The value $\beta$ and $\lambda c$ were estimated on the basis of the results of the dc-SHG measurement and the absorption spectrum. Examples of the results are shown in Table 4.

TABLE 4

| | $\beta(\times 10^{-30} \text{esu})$ | $\lambda c(\text{nm})$ |
|---|---|---|
| xanthone | 2.05 | 360 |
| 2-nitroxanthone | −7.95 | 380 |
| 3-nitroxanthone | 8.0 | 395 |
| 2,7-dinitroxanthone | 6.0 | 380 |
| 6-amino-1-nitroxanthone | 10.4 | 408 |

EXAMPLE 6

The following is a preparation example of a transparent polymer containing in the structure a xanthone derivative containing at least one electron withdrawing or one electron donating group.

14.6 Grams of 1-chloro-7-hydroxy nitroxanthone were dissolved in 200 ml of methylene chloride and an equivalent amount of methacryl chloride (6.1 g) was added gradually through a dropping funnel while cooling the mixture with water. Six hour-stirring gave an ester compound. A non linear optical medium in film state was obtained by heat polymerizing the compound while applying thereto a voltage of 100 kV/cm between bases equipped with an electrode. The medium thus obtained was made into an element. The conversion efficiency of the second harmonic wave of YGA laser was determined. The result was that the efficiency was 2 times that of urea.

EXAMPLE 7

The following is a preparation example of a transparent polymer as a composition (mixture) containing a xanthone derivative containing at least one electron withdrawing group or one electron donating group. After dissolving 5 g (0.021 mol) of 2-nitroxanthone in 50 g of methyl methacrylate and adding 0.02% of lauroyl peroxide, polymerization was carried out while applying a voltage of 100 kV/cm between the bases equipped with an electrode for 10 hours at 60° C. The polymerized composition thus obtained was made into element. The conversion efficiency of the second harmonic wave of YAG laser beams was determined in the same manner as described above. The result was that the efficiency was 15 times that of urea.

EXAMPLE 8

Table 5 shows the results of the calculation in regard to benzophenone skeletons. The molecular orbital was calculated by the CNDO/S3-CI method (CNDO: Complete Neglect of Differential Overlap, CI: Configuration Interaction) and then the lowest excited energy and hyperpolarizability $\beta$ were estimated.

TABLE 5

| No. | Molecular structure & Name | $\beta(10^{-30} \text{esu})$ | Lowest excited wavelength (nm) |
|---|---|---|---|
| A1 | benzophenone (diphenyl ketone) | $\beta_{YYY} = -2.3$  $\beta_{XXY} = 4.6$ | 285 |
| A2 | 4-methoxy-4'-nitro-benzophenone (CH$_3$O—C$_6$H$_4$—CO—C$_6$H$_4$—NO$_2$) | $\beta_{YYY} = -1.45$  $\beta_{XXX} = 9.3$ | 310 |
| R | 2-methyl-4-nitro-aniline (MNA) | $\beta_{YYY} = 9.0$ | 288 |

As has been described above, it was found that the benzophenone skeletons show a tendency of figuring an asymmetrical molecular arrangement from the calculation of the intermolecular energy.

The following table 6 shows the value $\beta$ and cutoff wavelength $\lambda$c which were estimated from dc-SHG (SHG: Second Harmonic Generation) and the SHG strength estimated from the powder SHG method relative to each sample.

TABLE 6

| No. | Name | $\beta_{eff}$ ($10^{-30}$ esu) | $\lambda$c (nm) | Powder SHG efficiency ($\times$ urea) |
|---|---|---|---|---|
| A1 | benzophenone | 2.0 | 360 | 0.8 |
| A2 | 4-methoxy-4'-nitrobenzophenone | 4.2 | 390 | 2.0 |
| R | 2-methyl-4-nitroaniline | 7.0 | 450 | 22.0 |

Figure 7:
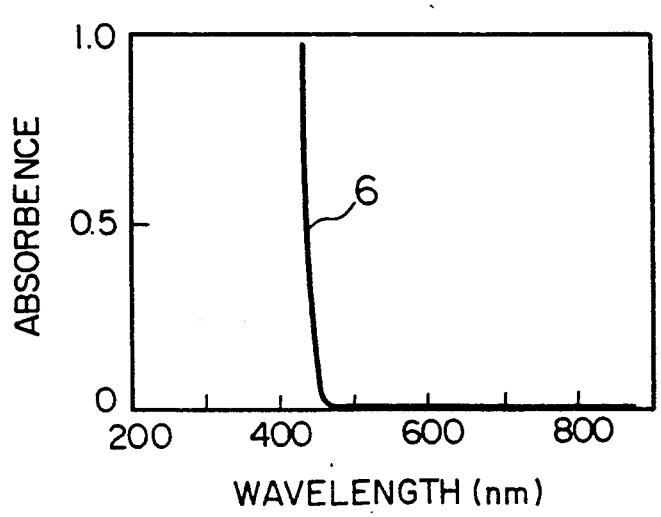
FIG. 7 is an absorption spectrum of 2-methyl-4-nitroaniline as a comparative example.
Figure 8:
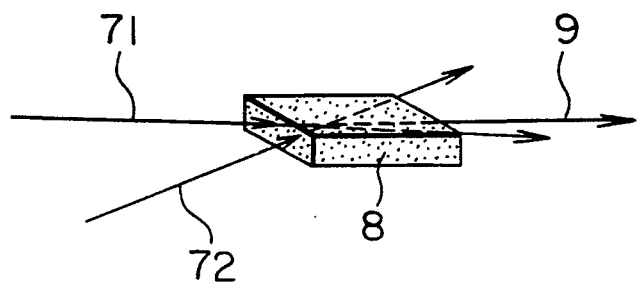
FIG. 8 is a schematic view of a frequency conversion element as another embodiment of the invention.
Figure 9:
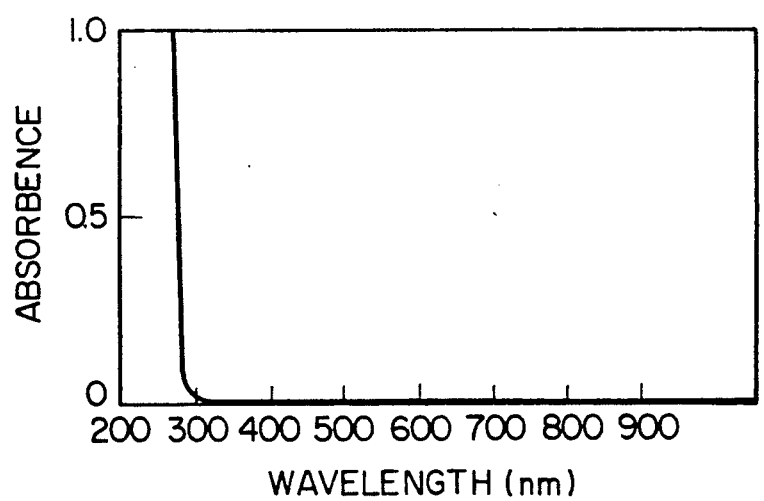
FIG. 9 shows an absorption spectrum of a compound of which substituents $R^3$ and $R^9$ shown in the formula (1) are methoxy group and nitro group, respectively.
Figure 10:
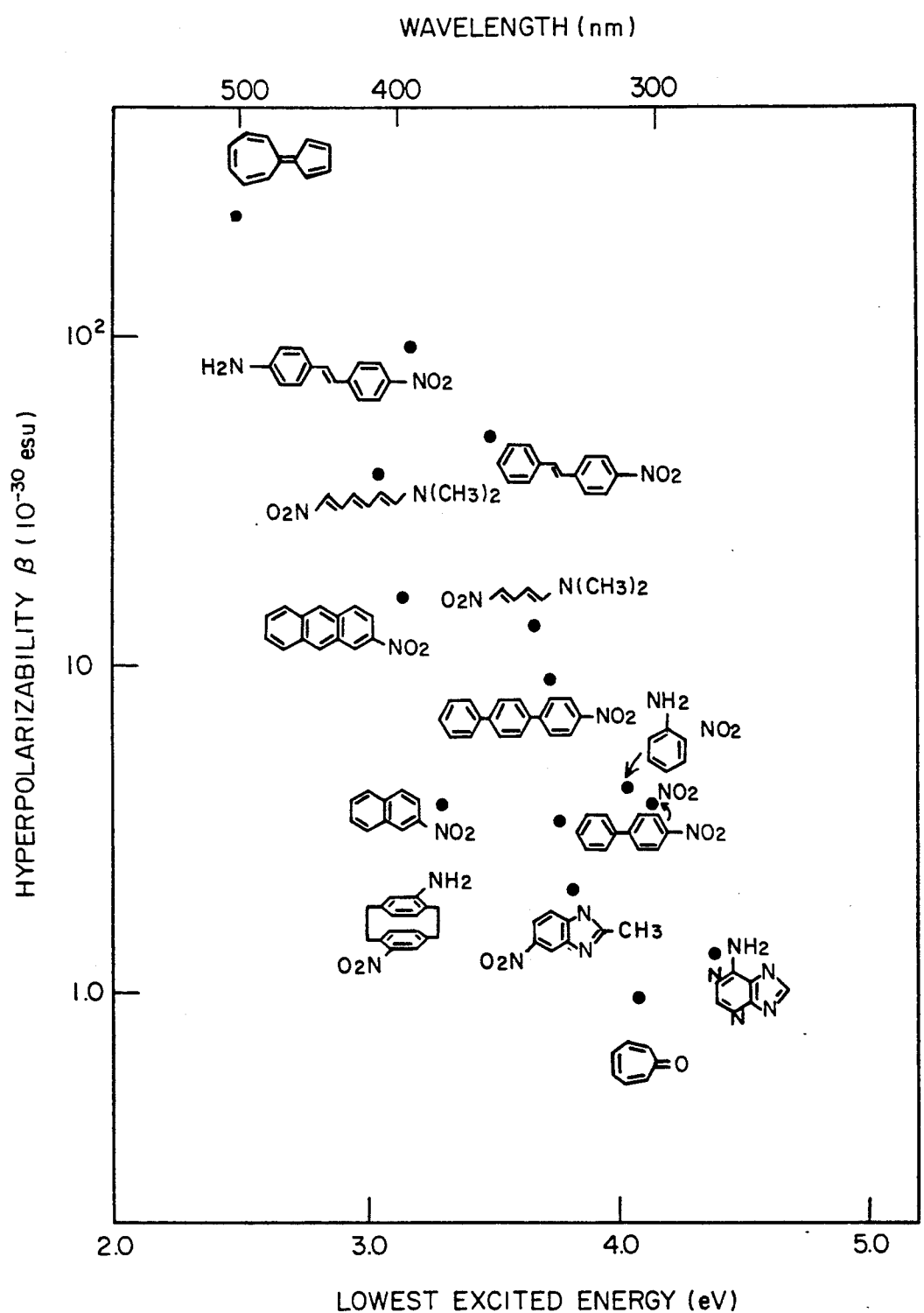
FIGS. 10 and 11 show the relationship among the lowest excitation energy, wavelength and hyperpolarizability $\beta$ of the second non-linear formation in a compound according to the invention.
Figure 11:
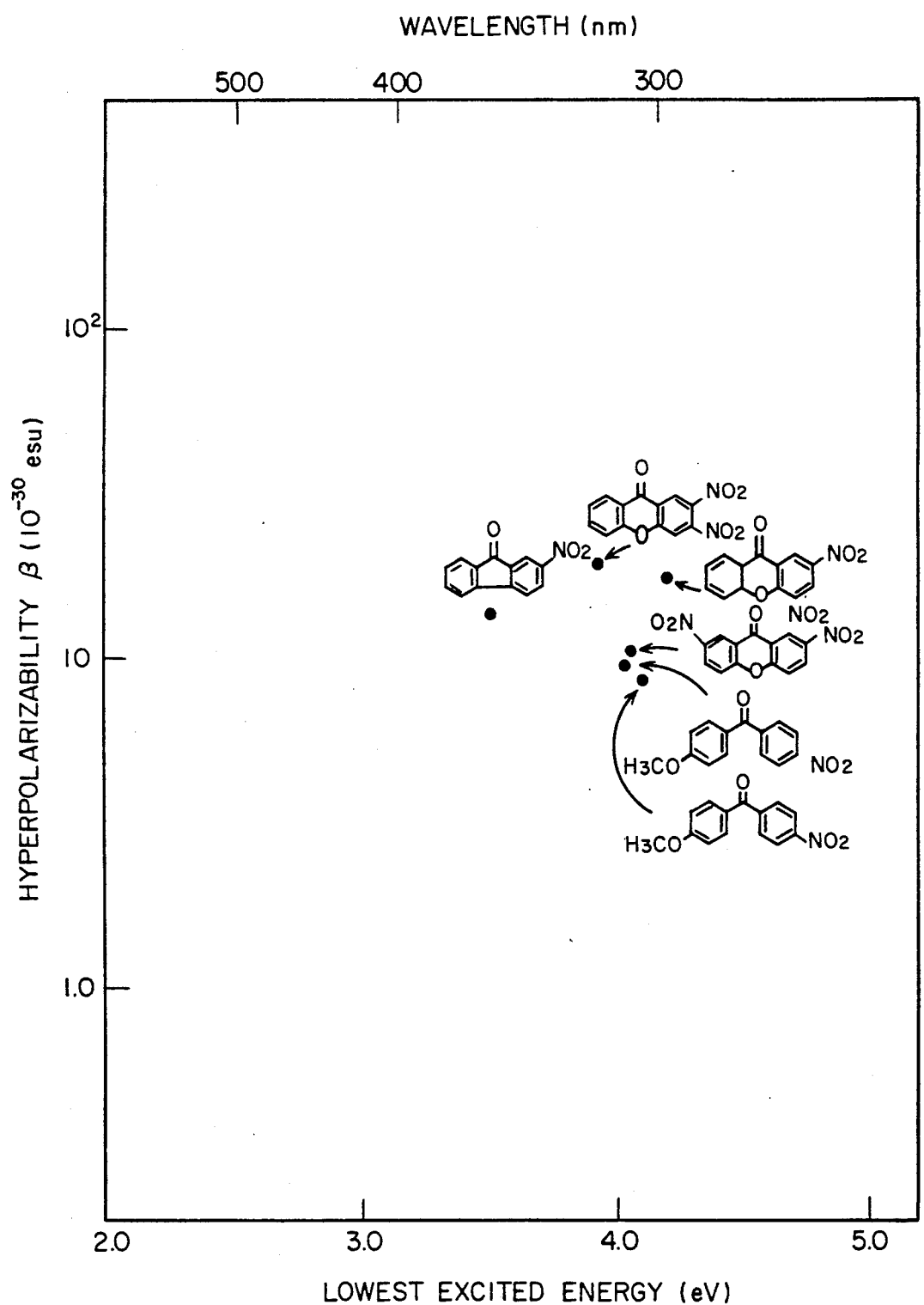

As for the dc-SHG, the ethanol solution which had been prepared for an sample, was charged into an optical cell made of two pieces of glass base having a transference electrode of ITO (ITO: Indium Tin Oxide) sticking together with a 5 mm spacer there. The measurement was carried out by irradiating laser beams when pulse voltage was applied. The measurement of the second harmonic wave (wavelength: 532 nm) was carried out with a photo-multiplier tube by making use of 5 kV, 2 $\mu$s of applied pulse voltage, a peak output of 100 MW of laser beams, and a Q switch YAG laser of 10 ns in pulse width (wavelength: 1064 nm). Nitrobenzene (liquid) was introduced into the similar optical cell and the output light was measured in the same manner. It was taken as a standard value. On the other hand, the sample was prepared in the form of 0.001 mol/l of ethanol solution for the measurement of cutoff wavelength and the absorption spectrum thereof was determined by a self-recording spectrophotometer. FIG. 6 shows the absorption spectrum of 4-methoxy-4'-nitrobenzophenone. FIG. 7 shows the absorption spectrum of the ethanol solution of 2-methyl-4-nitroaniline (MNA) having the same concentration as a comparative example. In the powder SHG method, the sample was made into pellet by pulverizing the sample in a mortar followed by pressing the same. They were irradiated by the above mentioned Q-switch YAG laser beams to carry out the measurement. Tables 5 and 6 show the results of the calculation and the observed data of the above-mentioned compounds and those of MNA for comparison.

As has been clear from the data of these examples and comparative examples, the non-linear optical device of the present invention has an excellent property in short cutoff wavelength, and is suitable as the materials for generating a second harmonic for the semiconductor laser converting an infrared light of 800 nm to 400 nm in wavelength. The non-linearity was equal to that of MNA and the conversion efficiency was extremely high.

EXAMPLE 9

Table 7 shows the cutoff wavelength $\lambda$c and strength of the powder SHG of other benzophenone derivatives.

TABLE 7

| No. | Name | $\lambda$c (nm) | Powder SHG efficiency ($\times$ urea) |
|---|---|---|---|
| A3 | 4-thiomethyl-4'-dimethyl-aminobenzophenone | 420 | 5.1 |
| A4 | 4-methoxy-4'-amino-benzophenone | 400 | 3.2 |
| A5 | 4-methoxy-4'-dimethyl-aminobenzophenone | 410 | 3.2 |

This example also had an excellent non-linearity as in the case with Example 8 and had properties suitable for the material for generating double waves for the semiconductor laser.

EXAMPLE 10

Frequency conversion element was made with 4-methoxy-4'-nitro benzophenone. FIG. 5 shows the schematic drawing. Single crystals of thin film 4-methoxy-4'-nitrobenzophenone were grown on a glass base by the liquid phase epitaxial growth method. The saturated ethanol solution of 4-methoxy-4'-nitrobenzophenone was prepared at 60° C. and gradually cooled (0.03° C./hr) in a constant temperature bath to obtain a 1 $\mu$m-thick film of single crystals. Double waves from a Q-switch YAG laser were irradiated to LiNbO₃ and parametrically oscillated. They were then penetrated into a non-linear optical device 2 as shown in FIG. 5 while continuously changing the wavelength between 1.1-1.3 μm. The strength of the second harmonic 4 which emits at a wavelength satisfying phase matching conditions was extremely increased. The conversion efficiency was estimated two times that of urea.

EXAMPLE 11

5.0 Grams of benzophenone were dissolved in 50 g of methyl methacrylate and 0.02% of lauroyl peroxide was added thereto. Polymerization was carried out for 10 hours at 60° C. The obtained laminar polymer was heated to 110° C., and then electric fields of 100 kV/cm was applied to the polymer clipped between the electrodes. After cooling the polymer down to room temperature again, basic waves from a YAG laser diverged into two beams were penetrated into the polymer and the strength of the radiated second harmonic wave was measured. The second-order non-linear optical constant $\chi^{(2)}$ determined from the result was $1.0 \times 10^{-12}$ m/V. This value is nearly the same value as that of KDP known as an inorganic non-linear optical material and is adequate for practical use. Furthermore, it is excellent in workability, and chemical and physical stability, because of the dispersion of benzophenone in polymethyl methacrylate.

EXAMPLE 12

The structure of the compounds listed in the aforementioned formula (1) was studied by the energy calculation method and the molecular orbital was calculated by the DNCO/S3-CI method (CNDO: Complete Neglect of Differential Overlap, CI: Configuration Interaction). The hyperpolarizability β and maximum exciting wavelength $\lambda_{max}$ of the molecules were calculated from the result of the above calculation. This example is shown in Table 8.

TABLE 8

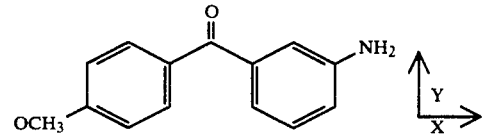

Then, each sample was examined by the dc-SHG (SHG: Second Harmonic Generation).

A sample was dissolved in ethanol and the solution was introduced in an optical cell which was made of two pieces of the glass base having a transference electrode of ITO (ITO: Indium Tin Oxide) sticking together with a 5 mm spacer therebetween. The measurement was carried out with the pulse voltage, especially with the irradiation of laser beams. The applied voltage was set at 5 kV, 2 μs, and Q-switch YAG laser beams (wavelength: 1064 nm) with a peak power of 100 MW, 10 ns was used as a laser to measure the strength of the frequency-converted light having a wavelength of 532 nm with a photomultiplier tube. The value β was estimated on reference to the output light of the pure liquid of nitrobenzene which was measured in the same manner.

Furthermore, 0.001 mol/l of ethanol solution was prepared and an absorption spectrum was determined with the same by a self-recording spectrophotometer. In the powder method, the sample was made into a pellet by pulverizing the sample in a mortar followed by pressing the same.

Table 9 shows β values determined by the dc-SHG method, the powder method and the absorption spectrum, the relative strength of a second harmonic wave of the powders based on that of urea (Powder eff. (X urea)) and the cutoff wavelength (λc) with comparative example.

TABLE 9

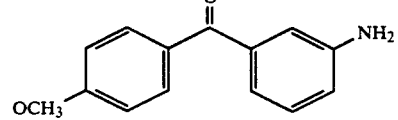

TABLE 9-continued

|  | $\beta(\times 10^{-30}\text{esu})$ | $E_{eff}(X \text{ urea})$ | $\lambda c(\text{nm})$ |
|---|---|---|---|
| [structure: 3-OCH₃ phenyl—C(=O)—phenyl-3-NO₂] | 5.9 | 2.2 | 322 |
| [structure: 4-OCH₃ phenyl—C(=O)—phenyl-3-NO₂] | 6.3 | 3.0 | 350 |

The cutoff wavelength of MNA, which has a large $\beta$, is around 480 nm and the absorption occurs in the visible region whereas the compounds of the present invention have a cutoff wavelength of less than 400 nm.

The media of the organic non-linear optical devices according to the present invention and of the specific meta-substituted benzophenone compounds satisfy the requirements as non-linear optical materials in all phases of non-linear optical capability, cutoff wavelength, and stability.

EXAMPLE 13

FIG. 1 shows a schematic drawing of frequency conversion elements which utilize the second harmonic generation. Specific meta-substituted benzophenone compounds encompassed in the aforementioned formula were used as non-linear optical media. The elements was made by make growing thin film monocrystals of the compounds on a base by liquid phase epitaxial growth method.

Second harmonic from the Q-switch YAG laser beams (wavelength: 1064 nm) having a peak power of 100 MW, 10 ns were irradiated to LiNbO₃ and the parametrically oscillated light was penetrated into the non-linear optical media as shown in FIG. 1 while continuously changing the wavelength between 1.1–1.3 μm. The strength of the second harmonic ($\lambda=532$ nm, frequency-converted light) was measured by a photomultiplier tube. The strength of the radiated second harmonic wave was extremely increased at a wavelength satisfying phase matching conditions. The conversion efficiency, when compared with that of urea, was approximately twice in the case the substituents $R^1$ and $R^2$ were methoxy group and nitro group in the compounds represented by the formula (1).

When the phase matching condition is applicable to the materials, the bulk crystals themselves can be made into elements. The crystals in this case, can be obtained by preparing a saturated butanol solution of the compound at 60° C. followed by slowly cooling the same to 10° C. in a constant temperature bath at a rate of 0.03° C. per hour.

EXAMPLE 14

The following is a preparation example of transparent polymers containing the compounds represented by the above formula as a composition.

5 Grams of the compound represented by the aforementioned formula (1) of which the substituents $R^1$ and $R^2$ are methoxy group and nitro group, respectively, were dissolved in 50 g of methyl methacrylate. After adding 0.02% by weight of lauroyl peroxide thereto, the polymerization was carried out for 48 hours at 60° C. The obtained polymer was heated at a temperature higher than the glass transition temperature (80° C.). The heated polymer was subjected to a poling made by a corona discharge for one hour. Then the resulting polymer was made into an element.

The conversion efficiency of the second harmonic wave of YAG laser determined in the same manner as in Example 13 was in the same level as that of urea. Due to the dispersion of the sample in polymethyl methacrylate, the material has excellent chemical and physical stabilities in processing.

The devices according to the present invention utilize fundamental characteristics of the non-linear optical materials and they can be utilized not only as frequency conversion elements utilizing the second harmonic wave described in the examples but as non-linear optical devices in a broad sense.

EXAMPLE 15

Table 10 shows the results of a similar test as that of Example 5 using the compounds listed in Table 10.

TABLE 10

|  | $\beta$(calculated) (XXX) $\times 10^{-30}$esu | Lowest excited wavelength (calculated) (nm) | $\beta$(observed) $\times 10^{-30}$esu | $\lambda c$(nm) | SHG efficiency (X urea) |
|---|---|---|---|---|---|
| [structure: 4-methyl-7-nitroxanthone] | −4.2 | 298 | 7.2 | 385 | 2.6 |

4-methyl-7-nitroxanthone

TABLE 10-continued

| | β(calculated) (XXX) ×10⁻³⁰esu | Lowest excited wavelength (calculated) (nm) | β(observed) ×10⁻³⁰esu | λc(nm) | SHG efficiency (X urea) |
|---|---|---|---|---|---|
| 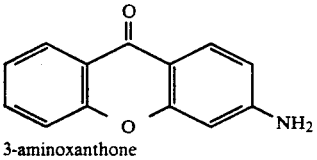 3-aminoxanthone | 3.7 | 329 | 4.0 | 400 | 5.0 |
| 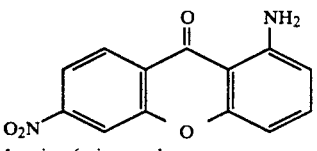 1-amino-6-nitroxanthone | −9.8 | 357 | 8.0 | 460 | 4.5 |
| 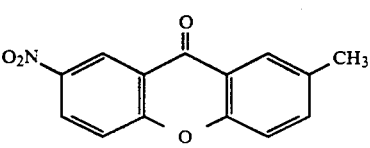 2-methyl-7-nitroxanthone | −4.2 | 298 | 7.0 | 390 | 4.0 |

EXAMPLE 16

Table 11 shows the results of a similar test as that of Example 8 using the compounds listed in Table 11.

TABLE 11

| | β(XXY) (calculated) (10⁻³⁰esu) | Lowest excited wavelength (nm) (calculated) | β(XXY) (observed) (10⁻³⁰esu) | λc(nm) | Powder SHG efficiency (X urea) |
|---|---|---|---|---|---|
| 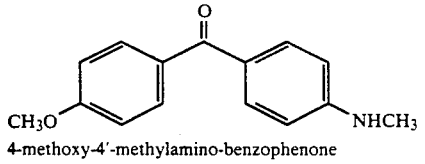 4-methoxy-4'-methylamino-benzophenone | 5.5 | 380 | 5.0 | 410 | 5.0 |
| 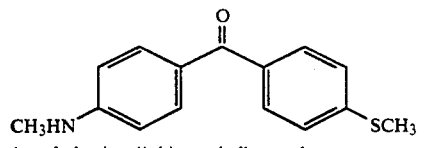 4-methylamino-4'-thio-methylbenzophenone | 6.0 | 390 | 4.4 | 420 | 3.0 |
| 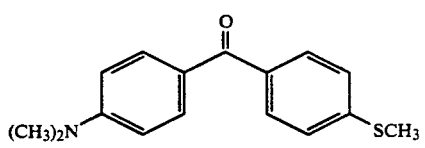 4-dimethylamino-4'-thio-methylbenzophenone | 4.6 | 380 | 4.0 | 420 | 5.0 |
| 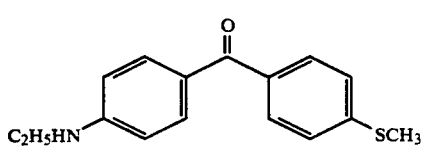 4-ethylamino-4'-thio-methylbenzophenone | 6.0 | 380 | 6.0 | 410 | 5.0 |

What is claimed is:

1. In a non-linear optical element device comprising a non-linear optical medium, the improvement, wherein the non-linear optical medium includes a compound exhibiting an SHG value equal to or larger than urea and having the general formula,

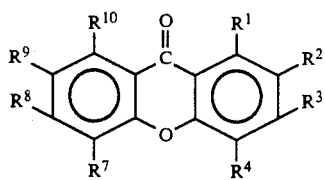

wherein at most two of $R^1$ and $R^4$ and at most two of $R^7$ to $R^{10}$ are substituents independently selected from the group consisting of —NO$_2$, —NH$_2$, —Cl, —Br, —OH, —CH$_3$ and —OCH$_3$, and the rest of $R^1$ to $R^4$ and $R^7$ to $R^{10}$ are hydrogen, the number of the substituents for $R^1$ to $R^4$ and $R^7$ to $R^{10}$ being one to three, provided that the total number of the substituents independently selected for $R^1$ to $R^4$ and $R^7$ to $R^{10}$ is one or two when each of the substituents independently selected is —NO$_2$.

2. A non-linear optical device according to claim 1, wherein the non-linear optical medium includes a transparent polymer.

3. A non-linear optical device according to claim 1, wherein said compound is 2-nitroxanthone.

4. A non-linear optical device according to claim 1, wherein the compound is selected from the group consisting of 1-nitroxanthone, 2-nitroxanthane, 3-nitroxanthone, 4-nitroxanthone, 6-amino-1-nitroxanthone, 6-amino-2-nitroxanthone, 5-methyl-2-nitroxanthone, 5-chloro-2-nitroxanthone, 2-bromo-1-nitroxanthone, 2-bromo-3-nitroxanthone, 1,7-dinitroxanthone, 2,7-dinitroxanthone, 2,4-dinitroxanthone, 2,7-diaminoxanthone, 1,3-dihydroxy-7-methoxyxanthone, 1-chloro-7-hydroxy-4-nitroxanthone, 1-chloro-7-methoxyxanthone, 4-methyl-7-nitroxanthone, 3-aminoxanthone, 1-amino-6-nitroxanthone, and 2-methyl-7-nitroxanthone.

5. A non-linear optical device according to claim 1, wherein the non-linear optical device includes a layer of material of the non-linear optical medium on a base.

6. A non-linear optical device according to claim 2, wherein the transparent polymer is oriented.

7. A non-linear optical device according to claim 2, wherein the transparent polymer is oriented by applying a direct current electric field at a temperature more than the glass transition temperature of the transparent polymer.

* * * * *